US008158429B2

(12) United States Patent
Tjioe

(10) Patent No.: US 8,158,429 B2
(45) Date of Patent: Apr. 17, 2012

(54) MULTICOLOR REAGENTS CONTAINING COMPENSATION CONTROLS

(75) Inventor: Iwan Tjioe, Fremont, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 401 days.

(21) Appl. No.: 12/501,630

(22) Filed: Jul. 13, 2009

(65) Prior Publication Data

US 2010/0028911 A1    Feb. 4, 2010

Related U.S. Application Data

(60) Provisional application No. 61/137,348, filed on Jul. 29, 2008.

(51) Int. Cl.
*G01N 33/543* (2006.01)
*G01N 31/00* (2006.01)
*G01N 21/76* (2006.01)

(52) U.S. Cl. ............ 436/10; 436/518; 436/546; 436/8; 436/15; 436/164; 436/166; 436/172; 435/7.1; 435/287.2; 422/430

(58) Field of Classification Search .................. 436/518, 436/523, 524, 525, 526, 527, 528, 529, 530, 436/531, 546, 44, 46, 172, 8, 10, 15, 164, 436/166; 435/6, 7.1, 287.2; 422/430
See application file for complete search history.

(56) References Cited

U.S. PATENT DOCUMENTS 7,507,588 B2 * 3/2009 Mehrpouyan et al. ........ 436/518
7,659,086 B2 * 2/2010 Harris et al. .................. 435/7.9

OTHER PUBLICATIONS

BD FACS 7-Color Setup Beads. 25 setups per kit—Catalog No. 335775: Feb. 1-8, 2007.

* cited by examiner

*Primary Examiner* — Gail R Gabel
(74) *Attorney, Agent, or Firm* — Douglas A. Petry

(57) ABSTRACT

The present invention provides multicolor reagent formulations containing in a single container both fluorescently labeled detection reagents and single-color compensation control reagents, wherein the compensation control reagents consist of reagent-capture particles bound to a fluorescently labeled detection reagent included in the multicolor reagent formulation. The multicolor reagent formulations of the present invention simplify manufacture and commercial distribution of multicolor reagent kits.

9 Claims, 2 Drawing Sheets

US 8,158,429 B2

MULTICOLOR REAGENTS CONTAINING COMPENSATION CONTROLS

CROSS-REFERENCE TO RELATED APPLICATIONS

The present application claims priority to U.S. provisional application Ser. No. 61/137,348, filed Jul. 29, 2008, which is incorporated herein by reference in its entirety.

BACKGROUND OF THE INVENTION

1. Field of the Invention

The present invention relates to the field of detection assays using fluorescent detection reagents. More particularly, the invention relates to fluorescent immunoassays, such as those carried out by flow cytometry.

2. Description of Related Art

Particle analyzers, such as flow and scanning cytometers, are well known in the art. In these systems, fluorescently labeled particles, such as molecules, analyte-bound beads, or individual cells, are individually analyzed by exposing each particle to an excitation light, typically one or more lasers, and measuring the resulting fluorescence from each of dye labels. Each particle may be labeled with a multiplicity of spectrally distinct fluorescent dyes. Typically, detection is carried out using a multiplicity of photodetectors, one for each distinct dye to be detected. Both flow and scanning cytometers are commercially available from, for example, BD Biosciences (San Jose, Calif.).

In flow cytometers and other instruments that employ a multiplicity of photodetectors to detect a multiplicity of dyes, the collected light is separated into specific ranges of wavelengths, typically by a system of frequency-dependent filters and dichroic mirrors, such that the light detected by a particular photodetector is limited to a predefined range of wavelengths, referred to as a detection channel. The detection channels and dyes are selected such that the peak of the emission spectrum of each dye is within the frequency range of a different detection channel, i.e., each detection channel detects primarily the emission from a single dye. However, because of the breadth of the emission spectra of fluorescent dyes, typically a dye will fluoresce in more than one detection channels and, thus, measurements of dye fluorescence are not independent. The emission of one dye in detection channels intended for the detection of other dyes is referred to by a number of terms, such as spillover, spectral overlap, and crosstalk.

Methods of decreasing the effect of spectral overlap on dye fluorescence measurements are known in the art. Such methods involve adjustment of the signal measured by each photodetector by an amount calculated to compensate for the contribution from dyes other than the primary dye to be detected. Examples in the field of flow cytometry include Bagwell et al., 1993, "Fluorescence Spectral Overlap Compensation for any Number of Flow Cytometer Parameters", Ann. N.Y. Acad. Sci. 677: 167-184; Roederer et al., 1997, "Eight Color, 10-Parameter Flow Cytometry to Elucidate Complex Leukocyte Hetrogeneity", Cytometry 29: 328-339; and Bigos et al., 1999, Cytometry 36: 36-45; Verwer, 2002, BD FACSDiVa™ Option for the BD FACSVantage SE Flow Cytometer White Paper, and U.S. Pat. No. 6,897,954; each incorporated herein by reference. WinList™ (Verity Software House, Topsham, Me.) and FlowJo 5.7.2 software (Tree Star, Inc., Ashland, Oreg.) are a stand-alone software packages that allow software compensation on stored data files produced by a flow cytometer.

Typically, the amount of fluorescence spectral overlap compensation required is determined experimentally using compensation control beads, single-color particles dye with one of the fluorescent dyes used in the assay. The fluorescence signal of each bead is measured in each of the channels, which directly provides a measure of the spectral overlap into each of the channels. Compensation control beads are intended to match the spectral characteristics of the detection reagent labeled with the same dye. However, the spectral properties of pre-dyed particles may provide only an approximation of the spectral properties of the detection reagent when used in a assay.

A preferred method of measuring spectral overlap of fluorescently labeled antibody reagents into each of the detection channels is using BD™ CompBeads compensation particles (BD Biosciences, San Jose, Calif.). The particles, which are coated with anti-Ig antibodies, are combined with a fluorescently labeled antibody reagent, which becomes captured on the surface of the bead, to produce a particle labeled with the fluorescent dye. The spectral overlap of the dye is determined by measuring the emission of the labeled particle in each of the detection channels. The measurement typically is made relative to the emission from the unlabeled particle. The use of the assay detection reagent itself to stain the single-color compensation control particle minimizes differences in spectral overlap between the compensation control particles and the assay reagent as used in the assay.

BD CompBeads compensation particles are not used directly with prepackaged multicolor reagents that comprise multiple fluorescently labeled detection reagents in a single container because each compensation particle needs to be stained with only one of the detection reagents, and, thus, the detection reagents cannot be mixed prior to staining the compensation particles. Although additional vials of each single-color detection reagent that comprise multicolor reagent could be provided to allow the use of BD CompBeads compensation particles, this would largely negate the advantages of providing premixed multicolor reagents.

BRIEF SUMMARY OF THE INVENTION

The present invention provides multicolor reagent formulations consisting of a plurality of fluorescently labeled detection reagents, wherein each of the plurality is distinctly labeled, and a plurality of single-color compensation control reagents. The compensation control reagents consist of reagent-capture particles bound to a fluorescently labeled detection reagent included in the multicolor reagent formulation.

The detection reagents, in general, can be any reagent that binds to a target of interest. In preferred embodiments, the fluorescently labeled reagents are antibodies, conjugated to fluorescent dyes, that are specific to an analyte, typically a protein, present in a sample. Analyte proteins may be present in any another form that permits optical analysis, such as present on or in cells, or as soluble proteins in a liquid sample.

Reagent-capture particles consist of particles having reagent-capture reagents bound to their surface. For each distinctly labeled species of detection reagent included in the multicolor reagent formulation, a corresponding compensation control reagent is formed by combining reagent-capture particles with the fluorescently labeled detection reagent under conditions such that fluorescently labeled detection reagent becomes bound to the surface of the reagent-capture particle. Because the single color compensation reagent is labeled with a fluorescently labeled detection reagent included in the multicolor reagent formulation, the spectral overlap measured from the compensation reagent accurately reflects the spectral overlap of the detection reagent itself.

In preferred embodiments in which the detection reagents are antibodies, the reagent-capture particles are particles having antibody-capture reagents bound to the surface of the particle. Preferred antibody-capture reagents are antibodies specific for an epitope present on the detector antibodies.

In a preferred embodiment, the single-color compensation control reagents are chemically stabilized to prevent dissociation of the reagent-capture particles and the detection reagent during storage. In preferred embodiments in which the detection reagents and reagent-capture reagent are proteins, such as antibodies, the compensation control particles are subjected to condition that result in the chemical cross-linking (e.g., fixing) of proteins. This cross-linking stabilizes the compensation control particle and prevents dissociation of the fluorescently labeled detection reagent from the capture reagent during storage.

The multicolor reagent formulations of the present invention contain both detection reagents and compensation control reagents; both are present during an assay. In order to carry out an assay with both types of reagents present, the signals measured from compensation control reagents should not interfere with the signals measured from the analyte-bound detection reagents. The two types reagents will be distinguishably identified by a combination of light scatter (e.g., forward scatter and side scatter) and fluorescent properties. For example, for cell analysis applications, reagent-capture particles bound to detection reagent will be distinguishable from cells bound to the same detection reagent by the different light scatter properties of particles versus cells.

The multicolor reagent formulations of the present invention can also be used with bead-based detection assays, such as BD Cytometric Bead Array assay (BD Bioscience, San Jose, Calif.), in which an analyte-capture particle is used to capture an analyte and a detection reagent is used to label analyte bound to the analyte-capture particle. In such applications, the reagent-capture particles will be selected to be distinguishable from the analyte-capture particles by an optical property such as light scatter. For example, the two types of particles can be selected to be of detectably different sizes.

The multicolor reagent formulations of the present invention provide a combination of properties that can be advantageous compared to currently used multicolor reagents formulations. Because each single-color compensation control reagent is stained with a fluorescently labeled detection reagent included in the formulation, the spectral properties of the control particle are matched to those of the corresponding detection reagent and lot-to-lot variability can be eliminated. This is particularly valuable if the reagent formulation includes detection reagents labeled with tandem fluorophores, such as PE-Cy5, PE-Texas Red®, PE-Cy7, and APC-Cy7, which exhibit marked lot-to-lot variability in their spectral properties. The multicolor reagent formulations of the present invention simplify the commercialization of multicolor reagents by eliminating the need for separate reagents for the measurements of spectral overlap. The multicolor reagent formulations of the present invention simplify manufacturing by enabling the staining and inclusion of compensation control particles to be carried out during the formulations stage.

DETAILED DESCRIPTION OF THE INVENTION

Figure 1:
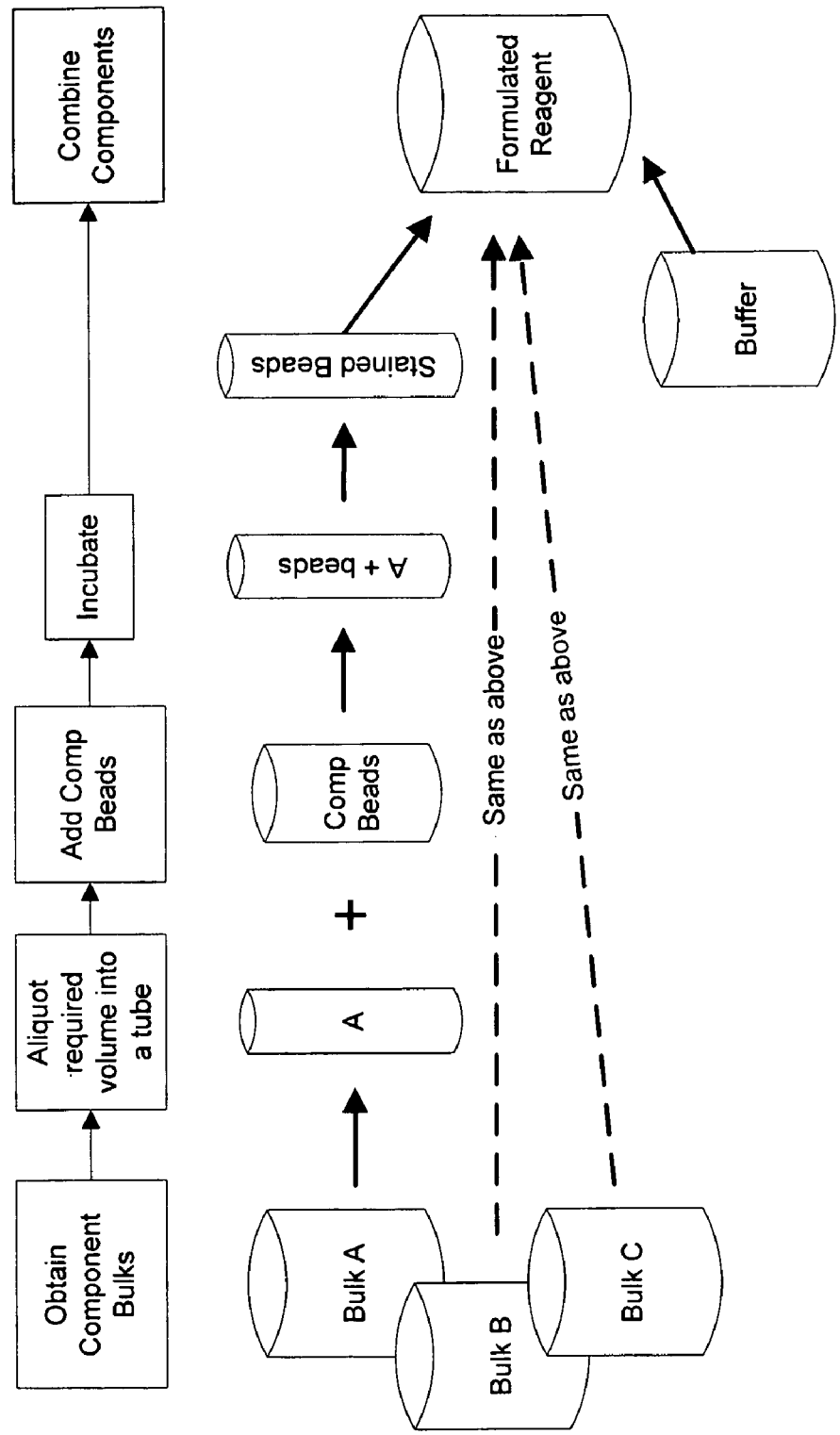
FIG. 1 provides a schematic of a manufacturing process of a multicolor reagent formulation of the present invention.
Figure 2:
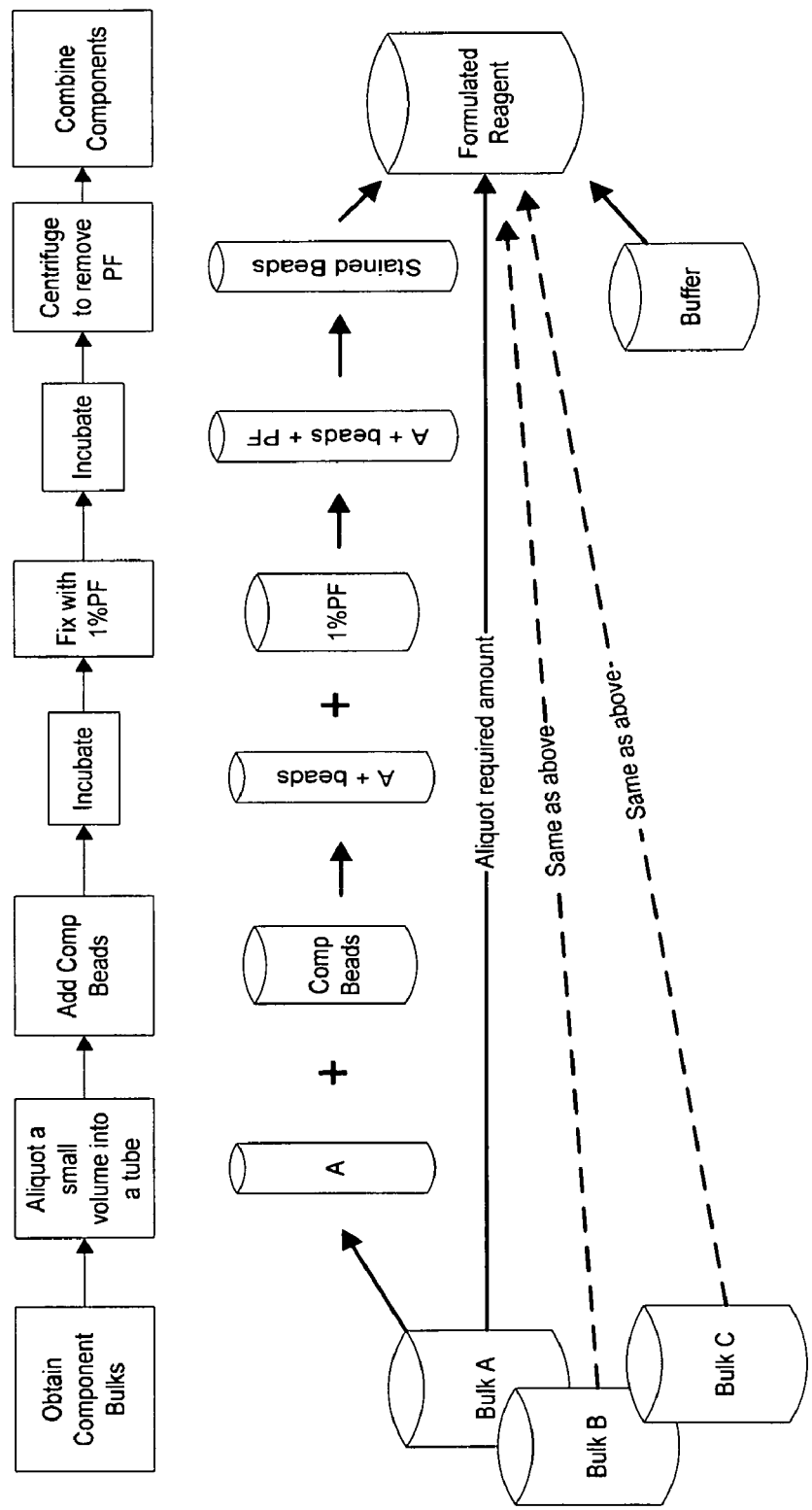
FIG. 2 provides a schematic of an alternative manufacturing process of a multicolor reagent formulation of the present invention.

The following definitions are provided for clarity. Unless otherwise indicated, all terms are used as is common in the art. All reference cited herein, both supra and infra, are incorporated herein by reference.

A "detector channel" or "detection channel" refers to the range of wavelengths that is detected by a specific photodetector. Typically, a plurality of non-overlapping detector channels are measured to facilitate the independent measurement of a plurality of spectrally distinct fluorescent dyes. The range of wavelengths detected typically is determined by the use of frequency-dependent filters and/or dichroic mirrors, as is well known in the art.

Typically, dyes and detector channels are selected such that, as much as is feasible, the emission maximum of each dye is within a different detector channel, i.e., such that each dye is matched to a detector channel optimized to detect light from that dye. However, due to the breadth of its emission spectrum, light from a given dye may be emitted within one or more other detector channels. The light emitted by a dye within a detector channel other than the detector channel that most closely matches the emission maxima of the dye is referred to herein as "spillover" or "spectral overlap".

The detector channel that most closely matches the emission maximum of a dye is referred to herein, with reference to the given dye, as the dye-detection channel or primary channel. All other detector channels are referred to, with reference to the given dye, as spillover channels or secondary channels. A dye and its dye-detection channel will be referred to as "corresponding" or "matched." With reference to a detection channel, the dye that corresponds to the detection channel is referred to as the primary dye; dyes that emit spillover into the detection channel are referred to as secondary dyes.

Compensation refers to the process of effectively removing from the total amount of light detected within a detector channel the contribution due to spillover from dyes other than the primary dye, i.e., the contribution from the secondary dyes. Thus, after compensation, the amount of light detected from a single detector channel represents a measure of the light emitted by a single dye, specifically, the primary dye. Compensation facilitates analysis of the data from multiply dyed particles by making the measurements of each of the dyes independent.

The term "analyte" is used herein broadly to refer to any substance to be analyzed, detected, measured, or labeled. Examples of analytes include, but are not limited to, proteins, peptides, hormones, haptens, antigens, antibodies, receptors, enzymes, nucleic acids, polysaccharides, chemicals, polymers, pathogens, toxins, organic drugs, inorganic drugs, cells, tissues, microorganisms, viruses, bacteria, fungi, algae, parasites, allergens, pollutants, and combinations thereof. By convention, where cells of a given cell type are to be detected, both the cellular component molecules or the cell itself can be described as an analyte.

As used herein an "analyte-specific reagent" or "target-specific reagent" broadly encompasses any reagent that preferentially binds to an analyte or target of interest, relative to other analytes potentially present in a sample. A target (analyte) and target-specific (analyte-specific) reagent are members of a binding pair, and either member of the pair can be used as the target-specific reagent in order to selectively bind to the other member of the pair. Examples of target and target-specific reagent pairs include, but are not limited to, antigen and antigen-specific antibody; hormone and hormone receptor; hapten and anti-hapten; biotin and avidin or steptavidin; enzyme and enzyme cofactor; lectin and specific carbohydrate; and complementary nucleic acid sequences. Preferred target-specific reagents are antibodies that include an antigen binding site that specifically binds (immunoreacts with) an antigen.

"Antibody", as used herein, includes all products, derived or derivable from antibodies or from antibody genes, that are useful as target-specific binding reagents in the cytometric methods described herein. "Antibody" thus includes, inter alia, natural antibodies, antibody fragments, antibody derivatives, and genetically-engineered antibodies, antibody fragments, and antibody derivatives.

As used herein, the terms "particles", "microparticles", and "beads" are interchangeable. These terms refer to small particles with a diameter in the nanometer to micrometer range, typically about 0.01 to 1,000 µm in diameter, preferably about 0.1 to 100 µm, more preferably about 1 to 100 µm, and, for use in flow cytometry, typically about 1 to 10 µm. Microparticles can be of any shape, but typically are approximately spherical ("microspheres"). Particles can be made of any appropriate material (or combinations thereof), including, but not limited to polymers such as polystyrene; polystyrene which contains other co-polymers such as divinylbenzene; polymethylmethacrylate (PMMA); polyvinyltoluene (PVT); copolymers such as styrene/butadiene, styrene/vinyltoluene; latex; or other materials, such as silica (e.g., SiO2).

Particles suitable for use in the present invention as a component of a compensation control reagent are well known in the art and commercially available from a number of sources, including: Bangs Laboratories (Carmel, Ind.), Interfacial Dynamics Corporation (Portland, Oreg.), Dynal (Great Neck, N.Y.), Polysciences (Warrington, Pa.), Seradyne (Indianapolis, Ind.), Magsphere (Pasadena, Calif.), Duke Scientific Corporation (Palo Alto, Calif.), Spherotech Inc. (Libertyville, Ill.) and Rhone-Poulenc (Paris, France). Chemical monomers for preparation of microspheres are available from numerous sources. For use in the present invention, the particles preferably are, within practical manufacturing tolerances, are of the same size, shape, composition, such that the particles exhibit the same, or nearly the same, optical properties. Consistent optical properties facilitates identifying and distinguishing the particles from stained analyte by their light scatter properties.

Detection Reagents

A detection reagent is used to facilitate optical detection of an analyte. Typically, a detection reagent comprises an analyte-specific reagent conjugated to a fluorescent label, such as a fluorescent dye or dye-containing particle. Fluorescent dyes are known to those of skill in the art and are commercially available from a number of sources. Suitable fluorescent dyes include, but are not limited to, phycoerythrin ("PE"), fluorescein isothiocyanate ("FITC"), allophycocyanin ("APC"), Texas Red ("TR", Molecular Probes, Inc.), peridinin chlorophyll complex ("PerCp"), CY5 (Biological Detection System) and conjugates thereof coupled to PE (e.g., PE/CY5, PE/APC and PE/TR); etc. A large number of dyes are commercially available from a variety of sources, such as, for example, Molecular Probes (Eugene, Oreg.), Exciton (Dayton, Ohio), and ABD Bioquest (Sunnyvale, Calif.).

Where the analyte-specific reagent is an antibody, the antibodies can be directly conjugated to a fluorescent label or can be labeled indirectly using a secondary antibody (e.g., a goat anti-mouse antibody conjugated directly to a fluorescent label) or by conjugating the antibody to one member of a binding pair (e.g., biotin) and using a dye conjugated to the other member of the binding pair (e.g., avidin or streptavidin). Direct conjugation is preferred, however, in many embodiments. A wide variety of fluorescently labeled antibodies suitable for use in the present invention are commercially available from, for example, BD Biosciences (San Jose, Calif.).

Alternatively, particularly for the detection of cells, the detection reagent may consist of a fluorescent compound that binds to a cellular component, either on the cell surface or intracellular. For example, the detection reagent is a "permeant dye" that is a light emitting compound capable of permeating cell membrane walls and binding to an intracellular molecule, such as a fluorescent nucleic acid binding compound.

Permeant dyes are known to those of skill in the art. Preferred permeant dyes are permeant fluorescent nucleic acid binding compounds that exhibit an increase in fluorescence upon binding to nucleic acid, such as, for example, thiazole orange and analogs thereof (such as those described in U.S. Pat. Nos. 4,883,867; 4,957,870; 5,656,449; each incorporated herein by reference); anthraquinone and derivatives thereof (such as DRAQ5™ and others described in U.S. Pat. No. 6,468,753, incorporated herein by reference); and SYTO® dyes (described in U.S. Pat. Nos. 5,436,134 and 5,534,416, both incorporated herein by reference), available from Molecular Probes (Eugene, Oreg.). Other useful permeant dyes include 4',6-diamidino-2-phenylindole (DAPI) and Hoechst stains.

Compensation Control Reagents

The compensation control reagents consist of reagent-capture particles bound to fluorescently labeled detection reagent. Each single-color compensation control reagent is labeled with one of the species of detection reagents included in the multicolor reagent formulation. Preferably, a complete set of compensation control reagents will be included in the multicolor reagent formulation, by which is meant that for each distinctly labeled species of detection reagent, there will be a corresponding single-color compensation control reagent. A complete set of single-color compensation control reagents enables measuring spectral overlaps for all the dyes included in the multicolor reagent formulation. However, depending on the application and fluorescent dyes used, it may be sufficient to include compensation control reagents for only a subset of the fluorescent dyes.

Reagent-Capture Particles

Reagent-capture particles consist of particles having reagent-capture reagents bound to their surface. The reagent-capture reagent functions to bind a fluorescently labeled detection reagent to the reagent-capture particle.

The reagent-capture reagent will depend on the type of detection reagents to be used. Preferably, the reagent-capture reagents bind to any of the detection reagents, regardless of the specificity of the detection reagent. This simplifies construction of the single-color compensation control reagents, as they can all be created using the same reagent-capture particles. The different single-color compensation control reagents are the product of reacting reagent-capture particles with each of the species of detection reagents in separate reactions.

Alternatively, reagent-capture reagents can be used that bind to detection reagents based on the specificity of the detection reagent. In one embodiment, the analyte itself can be used as the reagent-capture reagent. For example, for a detection reagent that is specific to a cell-surface molecule, the reagent-capture particle can be coated with the same molecule. The use of reagent-capture reagents that bind to detection reagents based on the specificity of the detection reagents requires the construction of a different reagent-capture reagent for each detection reagent. Although more complex to manufacture, this embodiment may provide improved long-term stability of the compensation control reagents when stored mixed in the multicolor reagent formulation. Even if dissociation of the reagent-capture particles and the detection reagent occurs during storage, the dissociated detection reagent can only re-associate with a reagent-capture particle having the same detection reagent specificity. Thus, dissociation and subsequent re-association of reagent-capture particles and detection reagents during storage will not result in reagent-capture particles bound to more than one species of detection reagent.

It will be understood that a combination of types of reagent-capture reagents, some that bind to multiple species of detection reagents independent of the specificity of the detection reagent, and some that bind based on the specificity of the detection reagent can be used. For example, if multiple antibody-based detection reagents are used in combination with a nucleic acid binding dye, then the reagent-capture reagents will necessarily be of different types.

In preferred embodiments, the detection reagents are fluorescently labeled antibodies, and reagent-capture reagent is an antibody that binds to an epitope present on a class of antibodies. Such antibodies that bind to classes of antibodies are well known in the art, and commonly used as secondary antibodies to label antigen-specific primary antibodies in immunoassays. In the present invention, such secondary antibodies are bound to the reagent-capture particle to form an antibody-capture particle.

Antibody-capture particles are commercially available. Preferred antibody-capture particles are BD CompBeads compensation particles (BD Biosciences, San Jose, Calif.), which consist of beads (particles) that have been coupled to an antibody specific for the Kappa light chain of Ig, from mouse, rat, or rat/hamster.

In embodiments that include as one of the detector reagents a fluorescent nucleic acid binding compound, a reagent-capture particle coated with double-stranded oligonucleotides can be used to capture the detector reagent.

Each compensation control reagent is created by combining reagent-capture particles with one species of a fluorescently labeled detection reagent under conditions such that the fluorescently labeled detection reagent becomes bound to the particles through the capture reagents. Suitable conditions are well known in the art. For example, conditions under which antibody detector reagents bind to antibody-capture particles are well known in the art and described in, for example, the BD CompBeads compensation particles instructions.

Stabilization of Compensation Control Reagents

The single-color compensation control reagents can be stabilized to improve long-term storage stability. Stabilization is preferred for embodiments in which the single-color compensation control reagents are made using reagent-capture reagents that bind to any of the detection reagents, regardless of the specificity of the detection reagent, such as using antibody-capture particles. In such embodiments, each different compensation control reagent is made by combining reagent-capture particles with one species of detection reagent in a separate reaction in order to obtain a single-color reagent. During long term storage of multiple single-color compensation control particles in the same suspension, reversible dissociation of the detection reagents from the particles can result in the gradual mixing of colors on the compensation control particles. Stabilization of the bond between the particles and the detector reagents can reduce this loss of particle label purity and improve long-term storage stability of the compensation control particles.

In preferred methods, the compensation control particles are stabilized to prevent dissociation of the reagent-capture particles and the detection reagent during storage by chemical cross-linking of the components. The particular chemical used to crosslink the components will depend on the detection reagent and reagent-binding reagent used. For the chemical cross-linking of proteins, the well known methods and chemicals used for fixing cells can be used. For example, cells prepared for analysis by flow cytometry typically are "fixed" by chemically cross-linking cellular components, such as proteins, using reagents that form covalent bonds between cellular components, such as aldehydes that form covalent cross-links between adjacent amine-containing groups on either proteins or nucleic acids. Formaldehyde is the most commonly used cross-linking fixative used to prepare cells for analysis by flow cytometry, and results in extensive crosslinking of proteins and nucleic acids throughout the cells. Formaldehyde is typically used at final concentrations of 1 to 4%. Although formaldehyde is commercially available in aqueous solution (referred to as formalin), because methanol typically is added to formalin to maintain the solubility of formaldehyde, it is preferable to prepare a solution prior to its use from paraformaldehyde, a polymeric form of formaldehyde available in powder form. Typically, the fixative is dissolved in a isotonic buffer so as to minimize osmotic stress on the cells. Phosphate-buffered saline (PBS) is a preferred buffer. Fixation reagents are commercially available from many sources.

Preferably, the compensation control reagents are washed following fixation to remove excess fixative. However, this wash step can be omitted if only a small amount of total compensation control reagents are included in the multicolor reagent formulation, as the effect of residual fixative will be minimal.

EXAMPLES

The present invention is additionally described by way of the following illustrative, non-limiting examples, that provide a better understanding of the present invention and of its advantages.

Example 1

Multicolor Reagent Formulation with Compensation Controls

A multicolor reagent was formulated to contain the fluorescently labeled detection antibodies: CD3-FITC, CD8-PE, CD45-PerCP, and CD4-APC (dye abbreviations are explained in the table, below). The multicolor reagent was formulated essentially as described above, with modifications as noted.

To generate single-color compensation control reagents, 23 µl of a 0.1 mg/ml CD3-FITC detection antibody, 8 µl of 0.0125 mg/ml CD8-PE detection antibody, 300 µl of 0.025 mg/ml CD45-PerCP detection antibody, and 153 µl of 0.006 mg/µl CD4-APC detection antibody were dispensed into separate tubes. To each tube was added 20 µL of antibody capture beads from a BD CompBeads compensation particles set (BD Biosciences, San Jose, Calif.), and the tubes were incubated at room temperature for 30 minutes. After staining, 1% paraformaldehyde was added to each of the four tubes to a final concentration of about 0.4%, and the tubes were incubated for 15 minutes to obtain four stabilized single-color compensation control reagents.

The single-color compensation control reagents combined in a single tube with 23 µl of a 0.1 mg/ml CD3-FITC detection antibody, 8 µl of 0.0125 mg/ml CD8-PE detection antibody, 300 µl of 0.025 mg/ml CD45-PerCP detection antibody to produce the final multicolor reagent formulation containing four detection reagents and four single-color compensation controls, referred to below as FORM 3.

In general, it may be desirable to centrifuge and wash the stained compensation-standard particles to remove any excess fixative prior to adding the compensation controls to the final reagent formulation. However, because the volume of compensation controls added to the final reagent formulation is small compared to the volume of detection reagents added, the effect of the residual fixative was expected to be minimal. For this reason, depending on the application, it may be adequate to omit the step of removing the residual fixative, as in the present experiments.

For comparison, a multicolor reagent was formulated from the four detection reagents, but without the compensation particles, referred to below as FORM 1.

Example 2

Cell Analysis

The multicolor reagent formulations of Example 1 (FORM 3 and FORM 1) were used to carry out the analysis of blood cells.

Flow Cytometer

The experiments were carried out using a BD FACSCalibur™ flow cytometer (BD Biosciences, San Jose, Calif.) with the four-color fluorescence detection option. This cytometer has two lasers, a blue laser (488 nm) and a red diode laser (~635 nm). Photomultiplier tubes (PMT) are used for measurement of dye fluorescence. The wavelength ranges detected for the measurement of forward scatter (FSC) and side scatter (SSC), and in each of the fluorescence detection channels (FL1-FL4), are shown in the table, below.

| Channel | Wavelength Range |
| --- | --- |
| FSC | 488/10 nm |
| SSC | 488/10 nm |
| FL1 | 530/30 nm |
| FL2 | 585/42 nm |
| FL3 | $\geq$670 nm |
| FL4 | 661/16 |

The detectors are intended to detect fluorescence from the following dyes as the primary dyes.

| Detector | Dye | Dye Abbreviation |
| --- | --- | --- |
| FL1 | fluorescein isothiocyanate | FITC |
| FL2 | phycoerythrin | PE |
| FL3 | peridinin chlorophyll protein | PerCP |
| FL4 | allophycocyanin | APC |

Instrument Setup

The PMT voltages in the flow cytometer were set for a Lyse/No-wash application according to the manufacturer's instructions using BD FACSComp™ software. Following the initial setup, all compensation settings were returned to zero so that the data obtained from the flow cytometer would be uncompensated (i.e., not adjusted for spectral overlap).

To obtain compensation values for use in cell analysis experiments using the FORM 3 multicolor reagent formulation, a sample of the FORM 3 multicolor reagent formulation (no cells) were analyzed by flow cytometry using the instrument described above. Similarly, to obtain compensation values for use in cell analysis experiments using the FORM 1 multicolor reagent formulation, compensation values were obtained using a BD CompBead compensation particle set stained using the separately formulated detection reagents, following the manufacturer's protocol.

The FORM 3 multicolor reagent formulation, as described above, was not formulated to contain a negative (unstained) compensation control particle. To provide a negative control in the experiments described herein, a separate negative control was created by adding to a tube containing 20 µL of FORM 3 multicolor reagent formulation and 450 µL of FACS Lysing Solution (BD Biosciences, San Jose, Calif.), one drop of negative CompBead control. This negative control tube was analyzed separately. In general, it is desirable to include such a negative control (BD CompBead compensation particle set do contain a negative control particle).

Analysis of Whole Blood

The FORM 3 and FORM 1 reagents were used to stain separate 50 µL samples of EDTA whole blood using the lyse-no-wash protocols, as published by BD Biosciences (San Jose, Calif.). To stain the sample, 20 µl of one of the reagents were added to the sample, the sample was incubated for 15 minutes at room temperature in the dark, 450 µl of FACS Lysing solution were added, and the sample was incubated for another 15 minutes at room temperature in the dark. Following staining, the samples were analyzed using the flow cytometer described above.

The data obtained were analyzed using FlowJo 5.7.2 software (Tree Star, Inc., Ashland, Oreg.). The data from the compensation control reagents were gated to isolate each of the singly-stained (and negative control) bead populations, and the spectral overlap of each single-color compensation control reagent was measured in each detection channel. The spectral overlap values obtained using the multicolor reagent formulation of the invention were essentially identical to the values obtained using BD CompBead compensation particles separately.

Compensation values were calculated from the spectral overlap measurements using the standard matrix algebra methods provided by the software. The compensation settings were then applied to the data obtained from the flow cytometric analysis of the stained blood samples. The compensated data were gated to isolate the CD45+ lymphocyte population, and the data from this subset were displayed on CD3 vs. CD4 and CD3 vs. CD8 bivariate plots. Quadrant gates were then applied and population frequencies in each quadrant were calculated. The table are shown in the following tables.

Frequency of Cell Subclass (CD3±, CD8±) among CD45+ lymphocytes

| Sample | CD3−, CD8+ | CD3+, CD 8+ | CD 3−, CD 8− | CD 3+, CD 8− |
|---|---|---|---|---|
| FORM 1 stained | 7.4 | 22.1 | 21.3 | 49.3 |
| FORM 3 stained | 7.0 | 21.1 | 22.2 | 49.7 |
| Difference | −0.3 | −1.0 | 0.9 | 0.5 |

Frequency of Cell Subclass (CD3±, CD4±) among CD45+ lymphocytes

| Sample | CD 3−, CD 4+ | CD 3+, CD 4+ | CD 3−, CD 4− | CD 3+, CD 4− |
|---|---|---|---|---|
| FORM 1 stained | 0.6 | 47.2 | 28.0 | 24.2 |
| FORM 3 stained | 0.9 | 47.2 | 28.2 | 23.7 |
| Difference | 0.3 | 0.0 | 0.3 | −0.5 |

The results demonstrate that the presence of the compensation control reagents in the multicolor reagent formulations of the present invention do not adversely affect the analysis of cells stained with the reagent. The single multicolor reagent formulation serves both for use as compensation controls and for staining cells for flow cytometric analysis. Thus, multicolor reagent formulations of the present invention provide a usable alternative to the current methods requiring separately provided compensation control particles.

I claim:

1. A multicolor reagent formulation comprising, prior to being added to a sample:
   (a) a plurality of fluorescently labeled analyte detection reagents, wherein each of said plurality is distinctly labeled; and
   (b) a plurality of single-color compensation control reagents, wherein each of said compensation control reagents consists of reagent-capture particles bound to one of said plurality of fluorescently labeled analyte detection reagents.

2. The multicolor reagent formulation of claim 1, wherein said fluorescently labeled detection reagents comprise an analyte-specific reagent conjugated to a fluorescent label.

3. The multicolor reagent formulation of claim 1, wherein said fluorescently labeled detection reagents comprise an antibody conjugated to a fluorescent label.

4. The multicolor reagent formulation of claim 3, wherein said reagent-capture particles are particles having antibody-capture reagents bound to the surface of the particles.

5. The multicolor reagent formulation of claim 4, wherein said antibody-capture reagents are antibodies specific for an epitope present on the detection reagents.

6. The multicolor reagent formulation of claim 5, wherein said single-color compensation control reagents are chemically stabilized to prevent dissociation of the reagent-capture particles bound to the fluorescently labeled detection reagent during storage.

7. The multicolor reagent formulation of claim 6, wherein said single-color compensation control reagents are chemically stabilized by exposure to condition that result in the chemical cross-linking of proteins.

8. The multicolor reagent formulation of claim 1, wherein said single-color compensation control reagents are chemically stabilized to prevent dissociation of the reagent-capture particles bound to the fluorescently labeled detection reagent during storage.

9. The multicolor reagent formulation of claim 8, wherein said single-color compensation control reagents are chemically stabilized by exposure to condition that result in the chemical cross-linking of proteins.

* * * * *